(12) United States Patent
Abdullah

(10) Patent No.: US 6,403,108 B1
(45) Date of Patent: Jun. 11, 2002

(54) COSMETIC COMPOSITION AND METHOD OF USE

(76) Inventor: Sheikh Ahmed Abdullah, 1385 Elm Cir., Fargo, ND (US) 58102

( * ) Notice: Subject to any disclaimer, the term of this patent is extended or adjusted under 35 U.S.C. 154(b) by 0 days.

(21) Appl. No.: 09/540,589

(22) Filed: Mar. 31, 2000

(51) Int. Cl.⁷ .............................. A61K 7/00; A61K 7/48
(52) U.S. Cl. ....................... 424/401; 424/616; 514/557; 514/159
(58) Field of Search ................................ 424/616, 401; 514/78, 159, 557

(56) References Cited

U.S. PATENT DOCUMENTS

| | | |
|---|---|---|
| 5,444,091 A | 8/1995 | Rapaport et al. |
| 5,607,980 A | 3/1997 | McAtee et al. |
| 5,612,324 A | 3/1997 | Guang Lin et al. |
| 5,652,228 A | 7/1997 | Bissett |
| 5,681,852 A | 10/1997 | Bissett |
| 5,760,079 A | 6/1998 | Shaffer et al. |
| 5,811,413 A | 9/1998 | Blank et al. |
| 5,814,662 A | 9/1998 | Znaiden et al. |
| 5,883,085 A * | 3/1999 | Blank et al. .................. 514/159 |
| 5,945,409 A * | 8/1999 | Crandall ....................... 514/78 |
| 6,071,541 A * | 6/2000 | Murad ......................... 424/616 |

* cited by examiner

Primary Examiner—Jose' G. Dees
Assistant Examiner—Mina Haghighatian
(74) Attorney, Agent, or Firm—Merchant & Gould P. C.

(57) ABSTRACT

A cosmetic composition is provided including between about 25 wt. % and about 55 wt. % Aloe vera gel, an effective keratolytic amount of alpha hydroxy acid to provide the composition with a pH between about 2.3 and about 3.7, and between about 5 wt. % and about 20 wt. % Vitamin C. A preferred alpha hydroxy acid is glycolic acid. A method for using the cosmetic composition is provided.

16 Claims, No Drawings

COSMETIC COMPOSITION AND METHOD OF USE

FIELD OF THE INVENTION

The invention relates to a cosmetic composition and to a method of using a cosmetic composition. In particular, the cosmetic composition includes between about 25 wt. % and about 55 wt. % Aloe vera gel, an effective keratolytic amount of alpha hydroxy acid to provide the composition with a pH between about 2.3 and about 3.7, and between about 5 wt. % and about 20 wt. % Vitamin C. The Vitamin C is preferably provided as encapsulated Vitamin C.

BACKGROUND OF THE INVENTION

The skin is subject to abuse by many extrinsic and environmental factors, as well as coronal aging or intrinsic factors. Common extrinsic factors include ultra violet radiation, pollutants, trauma and other exogenous agents and radiation. These extrinsic and intrinsic factors lead to wrinkling of skin. To many people, skin wrinkles are a reminder of aging. As a result, elimination of wrinkles has become an important concern in societal thinking.

Treatments for reducing wrinkles range from cosmetic creams and moisturizers to numerous forms of aesthetic surgery. Coronal aging results in the thinning and general degradation of skin. As the skin naturally ages, there is a reduction in the number of skin cells and blood vessels that supply the skin. There is also a flattening of the dermal-epidermal junction which results in weaker mechanical resistance to extraneous forces. As a consequence, aged people are more susceptive to blister formation, mechanical trauma and disease processes.

Combinations of various alpha hydroxy acids and humectants have been sold for many years. The use of these products has achieved some cosmetic improvement in wrinkles, skin turgor and tension of skin.

SUMMARY OF THE INVENTION

A cosmetic composition is provided by the invention. The cosmetic composition includes between about 25 wt. % and 55 wt. % Aloe vera gel, an effective keratolytic amount of alpha hydroxy acid to provide the composition with a pH of between about 2.3 and about 3.7, and between about 5 wt. % and 20 wt. % Vitamin C. The alpha hydroxy acid is preferably glycolic acid. The Vitamin C is preferably provided as encapsulated Vitamin C.

The cosmetic composition can include additional components. The cosmetic composition can include between about 0.1 wt. % and about 5 wt. % Vitamin A, and/or between about 0.05 wt. % and about 1 wt. % Vitamin E. In addition, the cosmetic composition can include a buffering agent to buffer the cosmetic composition to a pH of between about 2.3 and about 3.7. It should be appreciated that the amount of alpha hydroxy acid and buffering agent provided in the cosmetic composition is determined to provide the desired level of buffering at the desired pH. The cosmetic composition can additionally include conventional ingredients commonly found in cosmetic compositions including preservatives, colorants, fragrances, opacifiers, emulsifying agents, and stabilizers.

A method for using a cosmetic composition is provided by the invention. The method includes a step of applying the cosmetic composition to skin. The cosmetic composition is preferably applied to skin once or twice a day.

DETAILED DESCRIPTION OF THE PREFERRED EMBODIMENT

The present invention provides a cosmetic composition for treating the condition of coronal aging, such as wrinkling and fine lines, leathering, yellowing, sagging, hyperpigmentation and general signs of aging. The cosmetic composition enhances the general tone, glow and firmness of the skin.

The cosmetic composition according to the invention includes Aloe vera gel and an effective keratolytic amount of alpha hydroxy acid. The cosmetic composition preferably includes encapsulated Vitamin C. Encapsulated Vitamin C can be characterized as beads containing Vitamin C. After application of the cosmetic composition to skin, it is believed that the beads dissolve or rupture releasing the Vitamin C. Until the beads dissolve or rupture, the Vitamin C remains isolated from the alpha hydroxy acid. The cosmetic composition can additionally include Vitamin A and/or Vitamin E, and conventional ingredients commonly found in cosmetic compositions including preservatives, colorants, fragrances, opacifiers, emulsifying agents, and stabilizers.

The Aloe vera gel is preferably provided as a relatively pure grade of Aloe vera gel. Preferably, the Aloe vera gel is of a quality certified by the International Aloe Science Council. Aloe vera is generally recognized as a wound healing agent and is known to aid in the delivery of active ingredients to skin. The cosmetic composition according to the invention can be considered an Aloe vera based composition when Aloe vera gel is the largest single component of the composition. Preferably, the Aloe vera gel is provided in an amount which makes it the largest single component in the cosmetic composition. In general, it is desirable to provide as much Aloe vera gel in the cosmetic composition as possible. Preferably, the amount of Aloe vera gel provided in the cosmetic composition is between about 25 wt. % and about 55 wt. %, and more preferably between about 30 wt. % and about 50 wt. %, based on the weight of the cosmetic composition. Particularly preferred cosmetic compositions according to the invention include between about 48 wt. % and about 50 wt. % Aloe vera gel. It should be understood that the use of the phrase "wt. %" refers to the weight percent of a component based on the weight of the cosmetic composition.

The alpha hydroxy acid is generally provided in the cosmetic composition as a keratolytic agent for assisting in the exfoliation of skin. There should be a sufficient amount of alpha hydroxy acid to provide the cosmetic composition with desired exfoliation properties. In general, a sufficient amount of alpha hydroxy acid should be provided in the cosmetic composition to provide the cosmetic composition with a pH of about 3.7 or less. If the pH of the composition is greater than 3.7, the exfoliation property of the composition deteriorates. Preferably, the pH of the composition is sufficiently high so that the composition can be made available for home use and sold over the counter. Accordingly, the pH of the composition is preferably greater than about 2.3. When the alpha hydroxy acid is provided as a 70% active solution of alpha hydroxy acid, it is preferably provided in the cosmetic composition in an amount of about 15 wt. % In general, the amount of alpha hydroxy acid present in the cosmetic composition is sufficient to provide the composition, whether buffered or not buffered, with a pH of between about 2.3 and about 3.7. A preferred alpha hydroxy acid which can be used according to the invention is glycolic acid. Conventional cosmetic buffering agents can be used in the cosmetic composition according to the invention to provide the cosmetic composition with a pH of between about 2.3 and about 3.7.

Vitamin C is provided for enhancing skin collagen metabolism and rejuvenation. Accordingly, Vitamin C is provided in the cosmetic composition in an amount sufficient to provide the desired level of skin collagen metabolism and rejuvenation, but should not be provided in an amount which causes a reduction of the presence of other beneficial components. Preferably, the amount of Vitamin C provided in the cosmetic composition is between about 5 wt. % and about 20 wt. % and, more preferably, between about 10 wt. % and about 15 wt. % for Vitamin C having an active level of about 20%. In general, Vitamin C is commercially available as an aqueous solution containing 20% ascorbic acid.

Vitamin C tends to oxidize in the presence of an alpha hydroxy acid such as glycolic acid. According to the invention, the Vitamin C can be provided as encapsulated Vitamin C in order to reduce oxidation of the Vitamin C when provided in the cosmetic composition according to the invention. The encapsulated Vitamin C can be referred to as beads. A preferred type of beads containing Vitamin C can be referred to as Flourosome beads. It is believed that these beads either rupture or dissolve upon application to skin. It is believed that the rubbing of the beads into skin causes a warming of the beads causing them to dissolve or rupture. Once the beads dissolve or rupture, they release Vitamin C to the skin.

The cosmetic composition preferably includes Vitamin A for enhancing exfoliation and collagen activation. Vitamin A is an optional component in the cosmetic composition according to the invention, but, when it is present, it is preferably present at a concentration of between about 0.1 wt. % and about 5 wt. %, and more preferably between about 0.5 wt. % and about 3 wt. %. A preferred cosmetic composition according to the invention includes about 1 wt. % Vitamin A.

Vitamin E can be added to the cosmetic composition to enhance collagen stimulation and address scar tissue formation. Vitamin E is an optional component of the cosmetic composition according to the invention. If Vitamin E is incorporated into the cosmetic composition, it is preferably provided in an amount of between about 0.05 wt. % and about 1 wt. %. A preferred cosmetic composition according to the invention includes about 0.1 wt. % Vitamin E.

The cosmetic composition can include additional ingredients commonly used in cosmetic compositions. Exemplary additional components include preservatives, colorants, fragrances, and opacifiers. Preservatives can desirably be incorporated into the cosmetic composition to protect against the growth of potentially harmful microorganisms. Suitable preservatives which can be used include alkyl esters of parahydroxybenzoics. Other preservatives which can be used include hydantoin derivatives, propionate salts, and a variety of quaternary ammonium compounds. Particularly preferred preservatives include phenoxyethanol, methyl paraben, propyl paraben, imidazolidinyl urea, sodium dehydroacetate and benzyl alcohol. The preservative should be selected having regard for the use of the composition and possible incompatibilities between the preservatives and other ingredients. Preservatives are generally preferably employed in amounts ranging from 0.01 wt. % to 2 wt. % of the composition.

The cosmetic composition can be prepared by mixing the components together. In general, the encapsulated Vitamin C is added last and the cosmetic composition is gently mixed to avoid rupturing the beads.

The cosmetic composition according to the invention can be applied to skin and massaged gently into the skin. The cosmetic composition provides exfoliation of the skin. In general, it is expected that the cosmetic composition should be applied once or twice a day to particular areas of the skin.

The above specification provides a complete description of the manufacture and use of the composition of the invention. Since many embodiments of the invention can be made without departing from the spirit and scope of the invention, the invention resides in the claims hereinafter appended.

We claim:
1. A cosmetic composition comprising:
   (a) between about 25 wt. % and about 55 wt. % Aloe vera gel;
   (b) an effective keratolytic amount of alpha hydroxy acid to provide the composition with a pH between about 2.3 and about 3.7; and
   (c) between about 5 wt. % and about 20 wt. % Vitamin C.
2. A cosmetic composition according to claim 1, further comprising:
   (a) between about 0.1 wt. % and about 5 wt. % Vitamin A.
3. A cosmetic composition according to claim 1, wherein the alpha hydroxy acid comprises glycolic acid.
4. A cosmetic composition according to claim 1, further comprising:
   (a) between about 0.05 wt. % and about 1 wt. % Vitamin E.
5. A cosmetic composition according to claim 1, further comprising a buffering agent.
6. A cosmetic composition according to claim 1, further comprising a preservative.
7. A cosmetic composition according to claim 1, wherein the Aloe vera gel is provided in an amount of between about 30 wt. % and about 50 wt. %.
8. A cosmetic composition according to claim 2, wherein the Vitamin A is provided in an amount of between about 0.5 wt. % and about 3 wt. %.
9. A method for using a cosmetic composition, the method comprising:
   (a) applying a cosmetic composition to skin, the cosmetic composition comprising:
      (i) between about 25 wt. % and about 55 wt. % Aloe vera gel;
      (ii) an effective keratolytic amount of alpha hydroxy acid to provide the composition with a pH between about 2.3 and about 3.7; and
      (iii) between about 5 wt. % and about 20 wt. % Vitamin C.
10. A method according to claim 9, wherein the cosmetic composition further comprises between about 0.1 wt. % and about 5 wt. % Vitamin A.
11. A method according to claim 9, wherein the alpha hydroxy acid comprises glycolic acid.
12. A method according to claim 9, wherein the cosmetic composition further comprises between about 0.05 wt. % and about 1 wt. % Vitamin E.
13. A method according to claim wherein the cosmetic composition further comprises a buffering agent.
14. A method according to claim 9, wherein the cosmetic composition further comprises a preservative.
15. A method according to claim 9, wherein the Aloe vera gel is provided in an amount of between about 30 wt. % and about 50 wt. %.
16. A method according to claim 10, wherein the Vitamin A is provided in an amount of between about 0.5 wt. % and about 3 wt. %.

* * * * *